United States Patent
De La Poterie et al.

(10) Patent No.: US 6,946,123 B2
(45) Date of Patent: Sep. 20, 2005

(54) FILM-FORMING COSMETIC COMPOSITION

(75) Inventors: Valérie De La Poterie, Le Chatelet en Brie (FR); Nathalie Collin, Sceaux (FR); Bertrand Piot, Paris (FR)

(73) Assignee: L'Oreal, Paris (FR)

( * ) Notice: Subject to any disclaimer, the term of this patent is extended or adjusted under 35 U.S.C. 154(b) by 117 days.

(21) Appl. No.: 09/984,306

(22) Filed: Oct. 29, 2001

(65) Prior Publication Data

US 2003/0031640 A9 Feb. 13, 2003

(30) Foreign Application Priority Data

Oct. 27, 2000 (FR) .............................................. 00 13876

(51) Int. Cl.$^7$ ................................................ A61K 7/02
(52) U.S. Cl. ...................................... 424/70.7; 424/401
(58) Field of Search ............................... 424/70.7, 401, 424/61, 70.71, 707

(56) References Cited

U.S. PATENT DOCUMENTS

| | | | | |
|---|---|---|---|---|
| 5,389,363 | A | | 2/1995 | Snyder et al. |
| 5,858,338 | A | * | 1/1999 | Piot et al. ................... 424/70.7 |
| 5,866,111 | A | | 2/1999 | Felardos et al. |
| 5,911,973 | A | * | 6/1999 | de la Poterie ................. 424/61 |
| 6,106,813 | A | | 8/2000 | Mondet et al. |
| 6,113,925 | A | | 9/2000 | de la Poterie |
| 6,264,933 | B1 | * | 7/2001 | Bodelin et al. ............ 424/70.7 |
| 6,274,131 | B1 | | 8/2001 | Piot et al. |

FOREIGN PATENT DOCUMENTS

| | | |
|---|---|---|
| EP | 0 928 607 | 7/1999 |
| EP | 1 013 256 | 6/2000 |
| WO | WO 95/15741 | 6/1995 |
| WO | WO 96/33690 | 10/1996 |

OTHER PUBLICATIONS

Co-pending Application Title: Cosmetic Composition Comprising at Least One Fiber and at Least One Wax Inventor(s): Bertrand Piot et al. U.S. Filed: Oct. 29, 2001.

Leon M. Prince, "Microemulsions: Theory and Practice", Academic Press, 1977, pp. 21–32.

Charles M. Hansen, "The Three Dimensional Solubility Parameter—Key to Paint Component Affinities: I. Solvent, Plasticizers, Polymers, and Resins", Journal of Paint Technology, vol. 39, No. 505 Feb. 1967, pp. 104–117.

English language Derwent Abstract of EP 0 847 753, Jun. 17, 1988.

English language Derwent Abstract of EP 1 031 342, Aug. 30, 2000.

* cited by examiner

Primary Examiner—Jyothsna Venkat
(74) Attorney, Agent, or Firm—Finnegan Henderson Farabow Garrett & Dunner, L.L.P.

(57) ABSTRACT

The invention relates to methods for the make-up to and care of a keratinous material comprising applying to a keratinous material a composition comprising an aqueous microdispersion of particles of at least one wax and an aqueous dispersion of particles of at least one film-forming polymer. The composition makes it possible to obtain a film which may be resistant to cold water and may be removed as make-up with hot water.

The invention also relates to a mascara comprising an aqueous microdispersion of particles of at least one wax and an aqueous dispersion of particles of at least one film-forming polymer wherein the particles of at least one film-forming polymer have a mean particle size of at least 10 nm and further wherein the at least one film-forming polymer is not a coloring polymer and methods for application of the mascara.

86 Claims, No Drawings

FILM-FORMING COSMETIC COMPOSITION

The present invention relates to a method for forming a film comprising applying to a keratinous fiber a cosmetic composition comprising at least one film-forming polymer and at least one wax.

The present invention also relates to a mascara comprising, in a physiologically acceptable medium comprising an aqueous phase: an aqueous microdispersion of particles of at least one wax, and an aqueous dispersion of particles of at least one film-forming polymer.

The present invention also relates to a method for forming a film comprising applying to a keratinous fiber a cosmetic composition, in a physiologically acceptable medium, comprising at least one film-forming polymer and at least one wax, wherein the film formed on the keratinous material has good resistance to cold water and can be removed with hot water.

In another embodiment, the invention relates to a method of using make-up or care of keratinous fibers comprising applying to the keratinous fibers a cosmetic composition, such as for example, a mascara, comprising at least one film-forming polymer and at least one wax.

The keratinous materials used in the method of using make-up or care in accordance with the invention may be chosen, for example, from skin, eyelashes, eyebrows, hair and nails. The keratinous materials may be, for example, human keratinous materials. The cosmetic composition applied in the method of using make-up or care of keratinous materials may be in the form chosen, for example, from a mascara, an eyeliner, a product for the lips, a blusher, an eyeshadow, a foundation, a make-up product for the body, a concealer, a product for the nails, a composition for protecting against sunlight, a skin coloring composition, and a skincare product. In one embodiment of the invention, the composition is a mascara.

For the purposes of this invention, the expression "mascara" is understood to mean a composition which may be applied to eyelashes and may be chosen, for example, from a make-up composition for eyelashes, a make-up base for eyelashes, a composition to be applied over a mascara, also called top coat, and a composition for the cosmetic treatment of eyelashes. In one embodiment of the invention, the mascara may be applied to human eyelashes or to false eyelashes.

Mascara compositions in the form of a wax-in-water emulsion comprising surfactants are known from document WO-A-95/15741. However, this make-up film obtained with these compositions may not show good water resistance and when the film may come into contact with water, for example when bathing or taking a shower, it may partially disintegrate by crumbling or by spreading around the eye. The disintegration of the film may give rise to a substantial reduction in the intensity of the color of the make-up, thus obliging the consumer to repeat the application of the mascara. Spreading of the film may form a very unsightly halo around the area where make-up has been applied. Tears and perspiration also cause these same drawbacks.

To promote the water resistance of the make-up, it is known practice from U.S. Pat. No. 4,423,031 to use acrylic polymers in aqueous dispersion. However, the mascara may be difficult to remove and may require special make-up removers comprising oils or organic solvents. These make-up removers may be irritating to eyes, for example, they may cause pricklings (stinging), may leave a film over the eye, or may leave an uncomfortable fatty residual film on the skin around the eye (eyelids).

To avoid the use of these specific make-up removers, it is possible to use water and soap as described in document WO-A-96/33690, with a mascara comprising a water-insoluble polymer and a water-soluble film-forming polymer. However, the use of soap may cause ocular discomfort due to pricklings (stinging) or by deposition of a film over the eye. Soap may also solubilize the make-up film, which can then spread around the eyes to form unsightly halos and skin stains.

The use of hot water, that is to say, water having a temperature of at least 35° C. (temperature measured at atmospheric pressure), ranging, for example, from 35° C. to 50° C., makes it possible to avoid the drawbacks of the make-up removers known up until now. However, the cold-water-resistant mascara compositions described previously can be difficult to remove with hot water.

The present invention relates to a cosmetic composition which may be removed with hot water and may have good cold-water resistance.

The inventors have discovered that such a cosmetic composition may be obtained using an aqueous dispersion of particles of at least one film-forming polymer and a microdispersion of at least one wax.

After applying the cosmetic composition to the keratinous materials, for example, eyelashes, the make-up obtained exhibits: at least one of the following properties: good resistance to cold water (water with a temperature of less than or equal to 30° C., for example, when bathing), resistance to tears, and resistance to perspiration. The make-up can be easily removed with hot water, for example, by rubbing with cotton wool or gauze. The make-up can peel off easily from the eyelashes and be removed from the eyelashes in a form chosen, for example, from a non-fragmented coating layer, fragments and pieces. The make-up thus removed does not spread on the skin, avoiding the formation of halos around the eye. Thus, when removing the make-up, the skin is not stained and remains clean. The make-up may be removed simply with hot water, for example, with hot water containing no detergent agent such as soap. For the make-up removal, the hot water used may be chosen, for example, from tap water, demineralized water and mineral water heated to a temperature of at least 35° C., such as for example, ranging from 35° C. to 50° C. There is already known from document EP-A-847753 a composition capable of being applied, for example, to the skin, the semimucous membranes and the mucous membranes, comprising an aqueous dispersion of particles of film-forming polymers and an aqueous dispersion of waxes.

One embodiment of the invention, is a method for forming a film comprising applying to a keratinous material a composition comprising, in a physiologically acceptable medium comprising an aqueous phase:

an aqueous microdispersion of particles of at least one wax, and an aqueous dispersion of particles of at least one film-forming polymer, wherein the film formed on the keratinous material has good resistance to cold water and can be removed with hot water.

One embodiment of the invention is a mascara comprising, in a physiologically acceptable medium comprising an aqueous phase:

an aqueous microdispersion of particles of at least one wax, and an aqueous dispersion of particles of at least one film-forming polymer, wherein said particles of at least one film-forming polymer have a mean particle size of at least 10 nm and further wherein said at least one film-forming polymer is not a coloring polymer.

Yet another embodiment of the invention is a cosmetic method of using make-up or nontherapeutic care of a keratinous material comprising:

applying to the keratinous material, such as for example, eyelashes, a mascara comprising, in a physiologically acceptable medium comprising an aqueous phase:
an aqueous microdispersion of particles of at least one wax, and
an aqueous dispersion of particles of at least one film-forming polymer,
wherein said particles of at least one film-forming polymer have a mean particle size of at least 10 nm and further wherein said at least one film-forming polymer is not a coloring polymer.

Yet another embodiment of the invention is a cosmetic method for make-up removal from a keratinous material comprising:

applying to a keratinous material a composition comprising, in a physiologically acceptable medium comprising an aqueous phase:
an aqueous microdispersion of particles of at least one wax, and
an aqueous dispersion of particles of at least one film-forming polymer, and
rinsing said keratinous material at least one time with hot water, wherein said hot water is heated to a temperature of at least 35° C.

For the purposes of this invention, the expression "physiologically acceptable" may be understood to include a medium which is compatible with keratinous materials, for example, a cosmetic medium.

The removal of make-up with hot water may be obtained using an aqueous microdispersion of at least one wax which may make the film more sensitive to water. That is, the film may be made fragile during contact with hot water and rubbing of the the film, for example, with fingers, a cloth or cotton wool, easily disintegrates the film thus detaching the film from its support.

A. The at Least One Film-Forming Polymer in Aqueous Dispersion

The composition according to the invention contains at least one film-forming polymer in the form of particles in aqueous dispersion, generally known as a latex or pseudolatex.

In the present invention, the expression "at least one film-forming polymer" is understood to mean a polymer capable of forming, on its own or in the presence of a film-forming aid, a continuous and adherent film on a support, for example, on keratinous materials, such as eyelashes.

In one embodiment of the invention, the at least one film-forming polymer in aqueous dispersion is not a coloring polymer, which excludes the polymers comprising at least one monomeric organic coloring.

Non-limiting representatives of the at least one film-forming polymer which can be used in the composition of the present invention, may be chosen, for example, from synthetic polymers, such as free-radical polymers and polycondensate polymers, and polymers of natural origin.

For purposes of this invention, the expression "free-radical film-forming polymer" may be understood to indicate a polymer obtained by polymerization of unsaturated monomers, such as ethylenically unsaturated monomers, each monomer being capable of homopolymerizing (in contrast to polycondensates).

The at least one film-forming free-radical polymer may be chosen from vinyl polymers and vinyl copolymers, such as for example, acrylic polymers.

The vinyl polymers may result from the polymerization of at least one monomer chosen from monomers with ethylenic unsaturation containing at least one acid group, esters of these acid monomers and amides of these acid monomers.

As a monomer with ethylenic unsaturation having at least one acid group, it is possible to use α, β-ethylenic unsaturated carboxylic acids chosen, for example from acrylic acid, methacrylic acid, crotonic acid, maleic acid and itaconic acid. In one embodiment of the invention, (Meth)acrylic acid and crotonic acid may be used, and in another embodiment, (meth)acrylic acid may be used.

The esters of acid monomers may be chosen, for example, from (meth)acrylic acid esters (also called (meth)acrylates), for example, alkyl (meth)acrylates, wherein the alkyl group is chosen from linear, branched, and cyclic ($C_1$–$C_{30}$) alkyls, such as for example, ($C_1$–$C_{20}$)alkyl (meth)acrylates, and further still ($C_6$–$C_{10}$) aryl (meth)acrylates, and hydroxyalkyl (meth)acrylates, such as, ($C_2$–$C_6$) hydroxyalkyl (meth)acrylates.

Non-limiting examples of alkyl (meth)acrylates which may be mentioned are those chosen from methyl methacrylate, ethyl methacrylate, butyl methacrylate, isobutyl methacrylate, 2-ethylhexyl methacrylate, lauryl methacrylate and cyclohexyl methacrylate.

Non-limiting examples of hydroxyalkyl (meth)acrylates which may be mentioned are those chosen from hydroxyethyl acrylate, 2-hydroxypropyl acrylate, hydroxyethyl methacrylate and 2-hydroxypropyl methacrylate.

Non-limiting examples of aryl (meth)acrylates which may be mentioned are those chosen from benzyl acrylate and phenyl acrylate.

The (meth)acrylic acid esters may be formed, for example, from ($C_1$–$C_{30}$) alkyl (meth)acrylates.

According to the present invention, the alkyl group of the esters may be chosen, for example, from fluorinated and perfluorinated alkyl groups, that is to say that some or all of the hydrogen atoms of the alkyl group may be substituted with fluorine atoms.

Non-limiting examples of amides of acid monomers which may be mentioned are those chosen from (meth) acrylamides, for example, N-alkyl(meth)acrylamides, such as, ($C_2$–$C_{12}$) alkyls. Non-limiting examples of N-alkyl (meth)acrylamides, which may be further mentioned are those chosen from N-ethylacrylamide, N-t-butylacrylamide, N-t-octylacrylamide and N-undecylacrylamide.

The vinyl polymers of the at least one film-forming polymer may also result from the homopolymerization or copolymerization of at least one monomer chosen from vinyl esters and styrene monomers. For example, these monomers may be polymerized with at least one acid monomer, esters thereof, and amides thereof, such as those mentioned above.

Non-limiting examples of vinyl esters which may be mentioned are those chosen from vinyl acetate, vinyl neodecanoate, vinyl pivalate, vinylbenzoate and vinyl t-butyl benzoate.

Styrene monomers which may be mentioned are chosen, for example, from styrene and α-methylstyrene.

The list of monomers given above is not limiting and it is possible to use any monomer known to a person skilled in the art entering into the categories of acrylic and vinyl monomers (including the monomers modified by a silicone chain).

Non-limiting representatives of acrylic film-forming polymers which may be used according to the invention may be chosen, for example, from those sold under the names NEOCRYL XK-90, NEOCRYL A-1070, NEOCRYL A-1090, NEOCRYL BT-62, NEOCRYL A-1079, and NEOCRYL A-523 by the company Avecia-Neoresins, DOW LATEX 432 by the company Dow Chemical, and DAITO-SOL 5000 AD by the company Daito Kasey Kogyo.

Non-limiting representatives of at least one film-forming polymer include at least one polycondensate chosen, for example, from polyurethanes, polyesters, polyester amides, polyesters with at least one fatty chain, polyamides and epoxy ester resins. In one embodiment of the invention polyurethanes are used.

In another embodiment of the invention, the at least one film-forming polymer is chosen from vinyl polymers, polyurethanes, polyesters and polyamides.

The polyurethanes may be chosen, for example, from anionic polyurethanes, cationic polyurethanes, nonionic polyurethanes, amphoteric polyurethanes, anionic polyurethane-acrylics, cationic polyurethane-acrylics, nonionic polyurethane-acrylics, amphoteric polyurethane-acrylics, anionic polyurethane-polyvinyl-pyrrolidones, cationic polyurethane-polyvinyl-pyrrolidones, nonionic polyurethane-polyvinyl-pyrrolidones, amphoteric polyurethane-polyvinyl-pyrrolidones, anionic polyester-polyurethanes, cationic polyester-polyurethanes, nonionic polyester-polyurethanes, amphoteric polyester-polyurethanes, anionic polyether-polyurethanes, cationic polyether-polyurethanes, nonionic polyether-polyurethanes, amphoteric polyether-polyurethanes, anionic polyureas, cationic polyureas, nonionic polyureas, amphoteric polyureas, anionic polyurea-polyurethanes, cationic polyurea-polyurethanes, nonionic polyurea-polyurethanes, and amphoteric polyurea-polyurethanes.

The polyurethanes may be, for example, at least one polymer chosen from aliphatic polyurethanes, cycloaliphatic polyurethanes, aromatic polyurethanes, polyurea-urethanes and polyurea copolymers comprising alone or in mixtures blocks chosen, for example from:

at least one block chosen from aliphatic origin, cycloaliphatic origin, and aromatic origin, an optionally branched silicone-containing block, chosen, for example, from polydimethylsiloxane and polymethylphenylsiloxane, and a block comprising fluorinated groups.

Additional non-limiting representatives of polyurethanes in accordance with the invention may also be formed, for example, from optionally branched polyesters, alkyds comprising active hydrogens which are modified by reaction with a compound chosen, for example, from diisocyanate and difunctional organic compounds containing a group chosen, for example, from dihydro, diamino and hydroxyamino groups, and further comprising at least one group chosen from a carboxylic acid group, a carboxylate group, a sulphonic acid group, a sulphonate group, a neutralizable tertiary amine group and a quaternary ammonium group.

Further non-limiting representatives of film-forming polyurethanes which may be used according to the invention, are those marketed under the names NEOREZ R-981, and NEOREZ R-974 by the company Avecia-Neoresins; AVALURE UR-405, AVALURE UR-410, AVALURE UR-425, AVALURE UR-450, SANCURE 875, SANCURE 861, SANCURE 878, and SANCURE 2060 by the company Goodrich; and IMPRANIL 85 by the company Bayer.

The polyesters may be obtained, in a known manner, by polycondensation of at least one dicarboxylic acid with polyols, such as for example, diols.

The at least one dicarboxylic acid may be chosen, for example, from aliphatic dicarboxylic acids, alicyclic dicarboxylic acids and aromatic dicarboxylic acids. There may be mentioned as examples of such acids those chosen from: oxalic acid, malonic acid, dimethylmalonic acid, succinic acid, glutaric acid, adipic acid, pimelic acid, 2,2-dimethylgutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers may be used alone or in combination with at least two dicarboxylic acid monomers. In one embodiment of the invention, these monomers may be chosen, for example, from phthalic acid, isophthalic acid, and terephthalic acid.

Non-limiting representatives of diols may be chosen, for example, from aliphatic diols, alicyclic diols, and aromatic diols. In one embodiment of the invention the diols may be chosen, for example, from: ethylene glycol, diethylene glycol, triethylene glycol, 1,3-propanediol, cyclohexanedimethanol and 4-butanediol. Other non-limiting examples of polyols may be chosen, for example, from glycerol, pentaerythritol, sorbitol, and trimethylolpropane.

The polyester amides may be obtained in a manner similar to the polyesters, by polycondensation of diacids with a nitrogen containing compound chosen, for example, from diamines and amino alcohols. Non-limiting representatives of diamines may be chosen, for example, from ethylenediamine, hexamethylene-diamine, meta-phenylenediamine and para-phenylenediamine. A non-limiting example of an aminoalcohol which may be used is monoethanolamine.

The polyesters may also comprise at least one monomer carrying at least one group —$SO_3M$, wherein M is chosen, for example, from a hydrogen group, an ammonium ion $NH_4^+$ and a metal ion chosen, for example, from $Na^+$, $Li^+$, $K^+$, $Mg^{2+}$, $Ca^{2+}$, $Cu^{2+}$, $Fe^{2+}$ and $Fe^{3+}$ ions. A bifunctional aromatic monomer comprising a group —$SO_3M$ may also be used, for example.

The aromatic ring of the bifunctional aromatic monomer also bearing a group —$SO_3M$ as described above may be chosen, for example, from benzene, naphthalene, anthracene, diphenyl, oxydiphenyl, sulphonyldiphenyl and methylenediphenyl rings. Examples of bifunctional aromatic monomers also bearing a group —$SO_3M$ which may be mentioned include: sulphoisophthalic acid, sulphoterephthalic acid, sulphophthalic acid, and 4-sulphonaphthalene-2,7-dicarboxylic acid.

In the compositions according to the invention, it is possible to use copolymers based on isophthalate/sulphoisophthalate, such as for example, copolymers obtained by condensation of diethylene glycol, cyclohexanedimethanol, isophthalic acid and sulphoisophthalic acid. Such polymers are sold, for example, under the trade name EASTMAN AQ by the company Eastman Chemical Products.

The film-forming polymer of natural origin, which can be optionally modified, may be chosen, for example, from shellac resin, sandarac gum, dammars, elemis, copals, and water-insoluble cellulosic polymers.

Non-limiting examples of polymers formed from free-radical polymerization of at least one free-radical monomer located inside and/or partially at the surface, of preexisting particles of at least one polymer chosen, for example, from polyurethanes, polyureas, polyesters, polyester amides and alkyds. These polymers are generally called "hybrid polymers."

The dispersion comprising at least one film-forming polymer may be prepared by persons skilled in the art on the basis of their general knowledge.

The size of the particles of the at least one film-forming polymer may range from 10 nm to 500 nm, such as, from 20 nm to 300 nm.

In one embodiment of the invention, the at least one film-forming polymer has a water uptake of less than or equal to 50%, such as, less than or equal to 40%, further still, less than or equal to 30%, and even further still less than or equal to 20%.

According to the present invention, the expression "water uptake of a film-forming polymer" is understood to mean the percentage of water absorbed by the polymer after immersing the polymer for 10 minutes in water at 20° C. The water uptake is measured by a layer 300 $\mu$m thick (before drying) deposited on a plate and then dried for 24 hours at 30° C. and at 50% relative humidity; pieces of about 1 cm$^2$ cut out of the dry film are weighed (measurement of the mass $M_1$) and then immersed in water for 10 minutes; after immersion, the piece of film is wiped to remove the excess water at the surface and then weighed (measurement of the mass $M_2$). The difference, $M_2-M_1$, corresponds to the quantity of water absorbed by the polymer.

The water uptake is equal to $[(M_2-M_1)/M_1]\times 100$ and is expressed as a percentage by weight of water relative to the weight of polymer.

The at least one film-forming polymer in aqueous dispersion may be present in the composition according to the invention in a dry matter content ranging, for example, from 1% to 60% by weight relative to the total weight of the composition, such as from 5% to 40% by weight, and further from 10% to 30% by weight relative to the total weight of the composition.

The composition according to the invention may further comprise at least one film-forming aid which promotes the formation of a film with the particles of at least one film-forming polymer. Non-limiting representatives of the at least one film-forming aid may be chosen, for example, from all compounds known to persons skilled in the art as being capable of fulfilling the desired function, such as compounds chosen from plasticizing agents and coalescing agents.

The aqueous phase of the composition may consist essentially of water and may also comprise a mixture of water and at least one water-miscible solvent chosen, for example, lower monoalcohols having from 1 to 5 carbon atoms, such as for example, ethanol and isopropanol, glycols having from 2 to 8 carbon atoms, such as for example, propylene glycol, ethylene glycol, 1,3-butylene glycol, and dipropylene glycol, ($C_3$–$C_4$) ketones, and ($C_2$–$C_4$) aldehydes. The aqueous phase (water and optionally at least one water-miscible organic solvent) may be present in the composition in an amount ranging, for example, from 5% to 95% by weight relative to the total weight of the composition.

B. The Wax Microdispersion

The composition according to the invention may comprise, moreover, an aqueous microdispersion of particles of at least one wax. For purposes of this invention, the expression "aqueous microdispersion of at least one wax" is understood to mean an aqueous dispersion of particles of at least one wax in which the size of said particles of at least one wax is less than or equal to 1 $\mu$m.

In the present invention, at least one wax is defined as a lipophilic compound which is solid at room temperature (25° C.), with a reversible change of solid/liquid state, having a melting point range, for example, from at least 30° C. to 120° C. By bringing the wax to the liquid state (melting), it is possible to make it miscible with oils and to form a microscopically homogeneous mixture. However, when the temperature of the mixture is brought to room temperature, recrystallization of the wax in the oils of the mixture may be obtained.

The melting point of the at least one wax may be measured using a differential scanning calorimeter (DSC), for example, the calorimeter sold under the name DSC 30 by the company METLER. A 15 mg sample of product placed in a crucible is subjected to a first rise in temperature ranging from 0° C. to 120° C., at the rate of heating of 10° C./minute, and is then cooled from 120° C. to 0° C. at a cooling rate of 10° C./minute. The sample is finally subjected to a second rise in temperature ranging from 0° C. to 120° C. at a heating rate of 5° C./minute. During the second rise in temperature, the variation of the difference in power absorbed by the empty crucible and by the crucible containing the sample of product is measured as a function of the temperature. The melting point of the compound is the value of the temperature corresponding to the summit of the peak of the curve representing the variation of the difference in power absorbed as a function of the temperature.

Wax microdispersions are stable dispersions of colloidal particles of wax, and are described, for example, in "Microemulsions Theory and Practice," L. M. Prince Ed., Academic Press (1977) pages 21–32, which is incorporated by reference herein.

One method that these wax microdispersions may be obtained is by melting wax in the presence of a surfactant and optionally a portion of water, and then gradually adding hot water while stirring. The intermediate formation of a water-in-oil type emulsion is observed followed by a phase inversion with final production of an oil-in-water type microemulsion. On cooling, a microdispersion of solid colloidal particles of wax is obtained.

Wax microdispersions may also be obtained by stirring the mixture of wax, surfactant and water using stirring means chosen, for example, from ultrasound devices, high-pressure homogenizers and turbines.

The particles of at least one wax in the microdispersion may have mean particle sizes of less than 1 $\mu$m (for example, from 0.02 $\mu$m to 0.99 $\mu$m), such as from less than 0.5 $\mu$m (for example, from 0.06 $\mu$m to 0.5 $\mu$m).

These particles may comprise at least one wax. In addition, these particles may further comprise (in addition to the at least one wax) a minor proportion of at least one compound chosen, for example, from oily fatty additives, pasty fatty additives, surfactants customary fat-soluble additives and customary fat-soluble active agents.

Non-limiting examples of the at least one wax which may be used in the composition according to the invention may be waxes which are solid and rigid at room temperature, chosen, for example, from waxes of animal origin, waxes of plant origin, waxes of mineral origin, and waxes of synthetic origin. The at least one wax may have a melting point ranging, for example, from 30° C. to 120° C., such as ranging from 45° C. to 120° C. The at least one wax may also have a hardness ranging, for example, from 0.05 MPa to 15 MPa, such as from 3 MPa to 15 MPa, further from 6 MPa to 15 MPa.

Hardness may be determined by measuring the compacting force measured at 20° C. using a texturometer sold under the name TA-TX2i by the company RHEO, equipped with a stainless steel cylinder having a diameter of 2 mm, moving at the measuring speed of 0.1 mm/s and penetrating into the wax at a penetration depth of 0.3 mm. To carry out the measurement of hardness, the wax is melted at a temperature equal to the melting point of the wax plus 20° C. The molten wax is poured into a container having a diameter of 30 mm and a depth of 20 mm. The wax is recrystallized at room temperature (25° C.) for 24 hours, and then the wax is stored for at least 1 hour at 20° C. before carrying out the measurement of hardness. The hardness value is the measured compacting force divided by the surface of the texturometer cylinder in contact with the wax.

In one embodiment of the invention, a microdispersion of at least wax chosen from polar waxes is used. For purposes of this invention, the expression "polar waxes" is understood to mean at least one wax containing chemical compounds comprising at least one polar group. The at least one polar group is well known to persons skilled in the art; and may be chosen, for example, from alcohols, esters and carboxylic acids. Polyethylene waxes, paraffin waxes, microcrystalline waxes, ozokerite and Fisher-Tropsch waxes do not form part of the polar waxes.

In one embodiment of the invention, at least one polar wax has a mean HANSEN solubility parameter, $\sigma_\alpha$ at 25° C., such that $\sigma_\alpha > 0$ $(J/cm^3)^{1/2}$ and better still $\sigma_\alpha > 1$ $(J/cm^3)^{1/2}$.

$$\delta_\alpha = \sqrt{\delta_p^2 + \delta_h^2}$$

where $\sigma_p$ and $\sigma_h$ are, respectively, contributions of the polar type and of the types including interactions specific to the Hansen solubility parameters.

The definition of the solvents in the three-dimensional solubility space according to HANSEN is described in the article by C. M. HANSEN: "The three-dimensional solubility parameters" J. Paint Technol. 39, 105 (1967)(the disclosure of which relating to the definitions of the HANSEN solubility parameters is specifically incorporated by reference herein):

$\sigma_h$ relates to the specific forces of interactions, such as for example, hydrogen bonding, acid/base and donor/acceptor type, and the like;

$\sigma_p$ relates to the DEBYE forces of interaction between permanent dipoles and the KEESOM forces of interaction between induced dipoles and permanent dipoles.

The parameters $\sigma_h$ and $\sigma_p$ are expressed in $(J/cm^3)^{1/2}$.

Polar waxes may be chosen, for example, from hydrocarbon waxes and waxes formed from catalytic hydrogenation of oils.

Non-limiting examples of polar waxes may include hydrocarbon waxes chosen, for example, from beeswax, lanolin wax, Chinese waxes, rice wax, Carnauba wax, candelilla wax, ouricury wax, cork fiber wax, sugarcane wax, Japan wax, sumac wax, montan wax, waxy copolymers and esters of waxes.

Other non-limiting representatives of polar waxes are those waxes obtained, for example, by catalytic hydrogenation of oils chosen, for example, from animal oils having linear and branched ($C_8$–$C_{32}$) fatty chains, and vegetable oils having linear and branched ($C_8$–$C_{32}$) fatty chains. Among these, there may be mentioned those oils chosen, for example, from hydrogenated jojoba oil, hydrogenated sunflower oil, hydrogenated castor oil, hydrogenated copra oil and hydrogenated lanolin oil.

Other examples of the at least one wax may include silicone waxes and fluorinated waxes.

In one embodiment of the invention carnauba wax, beeswax and candelilla wax may be used.

It is also possible to use commercial mixtures of self-emulsifiable waxes comprising at least one wax and at least one surfactant. These commercial mixtures make it possible to prepare microdispersions of at least one wax by simple addition of water.

The composition content of wax in the form of a microdispersion of at least one wax (called first wax), may be present in a dry matter content ranging, for example, from 0.1% to 50% by weight relative to the total weight of the composition, such as, from 1% to 30% by weight, and further still from 5% to 20% by weight relative to the total weight of the composition.

The composition may further comprise an effective quantity of at least one surfactant to make it possible to obtain a wax microdispersion, as well as a stable, final composition. For example, the composition in accordance with the invention may comprise at least one surfactant which is present in an amount ranging, for example, from 0.01% to 5% by weight relative to the total weight of the composition. The at least one surfactant may be chosen, for example, from the following compounds:

anionic surfactants chosen, for example, from optionally unsaturated fatty acid salts having from 12 to 18 carbon atoms, alkali metal salts of salts of organic bases with ($C_2$–$C_{18}$) alkylsulfuric acids, alkali metal salts of salts of organic bases with ($C_{12}$–$C_{18}$) alkylsulfonic acids, alkali metal salts of salts of organic bases with ($C_6$–$C_{18}$) alkylarylsulfonic acids, and ether sulfates;

nonionic surfactants, chosen, for example, from polyalkoxylated surfactants and polyglycerolated surfactants, such as fatty acids, fatty acid amides, fatty alcohols, alkylphenols; esters of fatty acids and polyols, alkanediols, alkyl ethers of alkanediols; and at least one compound chosen from alkyl carbamates of triglycerol, oxyethylenated derivatives of lanolin alcohols, propoxylated derivatives of lanolin alcohols, and lanolin fatty acids; and cationic surfactants, chosen, for example, from quaternary ammonium derivatives.

The at least one wax may be further combined with at least one fatty additive chosen, for example, from fatty oily additives, fatty pasty additives and fatty, oily and past additives. Non-limiting examples of at least one fatty additive may be chosen, for example, from vegetable oils such as sunflower oil and jojoba oil; mineral oils such as paraffin oil; silicone oils; petroleum jelly; lanolin; fluorinated oils; and hydrocarbon oils with at least one perfluorinated group; and esters of fatty alcohols.

It is possible to further introduce into the microparticulate waxy phase additional at least one fatty additives such as fat-soluble active ingredients chosen, for example, from UV-screening agents, fat-soluble vitamins, and fat-soluble cosmetic active agents.

In one embodiment of the invention, the composition may comprise the microdispersion of at least one wax and the at least one film-forming polymer in aqueous dispersion in a at least one film-forming polymer to a microdispersed at least one wax weight ratio ranging, for example, from 50:50 to 95:5, and such as from 60:40 to 80:20.

C. The Additives

The composition according to the invention may further comprise, in addition to the microdispersion of at least one wax, at least one additional wax in the form of particles having a particle size, for example, of at least 1 μm, such as, at least 1.3 μm, dispersed in the aqueous phase. This at least one additional wax does not therefore exist in the form of an aqueous microdispersion of particles of wax as defined above. In one embodiment of the invention, the mean particle size of the at least one additional wax may range, for example, from 1 μm to 10 μm, such as, from 1.3 μm to 5 μm.

The at least one additional wax may make it possible to obtain a thick application of make-up onto the eyelashes, it is then said that the make-up (mascara) has a high loading capacity. The composition according to the invention comprising the at least one additional wax may be used to thicken keratinous fibers, such as for example, eyelashes. This at least one additional wax may be chosen, for example, from the waxes cited above and may be present in the composition according to the invention in an amount ranging, for example, from 0% to 30% by weight, such as from 0.1% to 30% by weight, relative to the total weight of the composition. In one embodiment of the invention, the at least one additional wax is present in the amount ranging from 1% to 25% by weight, such as from 5% to 20% by weight relative to the total weight of the composition.

In one embodiment, the at least one film-forming polymer and the at least one additional wax may be present in the composition in an at least one film-forming polymer to at least one additional wax weight ratio ranging, for example, from 40:60 to 95:5, such as from 55:45 to 80:20.

The aqueous phase of the composition may further comprise at least one additional water-soluble film-forming polymer. The at least one additional water-soluble film-forming polymer may be present in the composition in an amount ranging, for example, from 0.01% to 5% by weight relative to the total weight of the composition.

As at least one additional water-soluble film-forming polymer, there may be mentioned those chosen, for example, from:
- water-soluble cellulosic polymers chosen, for example, from hydroxyethyl cellulose, hydroxypropyl cellulose, carboxymethyl cellulose, hydroxypropyl ethyl cellulose, and ethyl hydroxyethyl cellulose;
- keratin derivatives chosen, for example, from keratin hydrolysates and sulfonic keratins;
- compounds chosen, for example from anionic chitins, cationic chitins, amphoteric chitins, nonionic chitins and chitosan derivatives, such as hydroxypropyl chitosan;
- cellulose derivatives chosen, for example, from hydroxyethyl cellulose, hydroxypropyl cellulose, methyl cellulose, ethyl hydroxyethyl cellulose, carboxymethyl cellulose, and quaternized derivatives of cellulose;
- acrylic polymers and acrylic copolymers chosen, for example, from polyacrylates and polymethacrylates;
- compounds chosen from polyvinyl alcohols and polyvinylpyrrolidones;
- vinyl copolymers chosen, for example, from copolymers of methyl vinyl ether and malic anhydride, and copolymers of vinyl acetate and crotonic acid;
- polyethylene glycols;
- optionally modified polymers of natural origin chosen, for example from:
  - gum arabic, guar gum, xanthan derivatives, karaya gum; alginates, carrageenans, glycoaminoglycans, hyaluronic acid, hyaluronic acid derivatives, shellac resin, sandarac gum, dammars, elemis, copals, and deoxyribonucleic acid.

The composition according to the invention may further comprise at least one coloring agent chosen, for example, from pulverulent compounds. The at least one coloring agent may be present in the composition of the invention in an amount ranging, for example, from 0.01 to 50% by weight relative to the total weight of the composition. The pulverulent compounds may be chosen, for example, from pigments and pearlescent agents normally used in cosmetic and dermatological compositions.

In one embodiment of the invention, the pulverulent compounds may be present in the composition of the invention in an amount ranging, for example, from 0.1 to 25% by weight relative to the total weight of the composition, such as from 1 to 20% by weight relative to the total weight of the composition.

The pigments may be chosen from white and colored, inorganic and organic, pigments. Non-limiting examples of inorganic pigments may be chosen from titanium dioxide, optionally surface-treated zirconium oxides, optionally surface-treated cerium oxides, iron oxides, chromium oxides, manganese violet, ultramarine blue, chromium hydrate and ferric blue. Non-limiting examples of organic pigments may be chosen from carbon black, D & C type pigments, and lacquers based on units chosen, for example, from carmine, barium, strontium, calcium and aluminium.

Pearlescent pigments may be chosen, for example, from white pearlescent pigments, such as mica coated with titanium, and mica coated with bismuth oxychloride, colored pearlescent pigments, such as for example, mica-titanium with iron oxides, mica-titanium with, for example, ferric blue or chromium oxide, mica-titanium with an organic pigment of the abovementioned type and pearlescent pigments based on bismuth oxychloride.

The composition in accordance with the invention may further comprise at least one filler which may be chosen, for example, from those well known to persons skilled in the art and which are commonly used in cosmetic compositions. The at least one filler may be lamellar and spherical fillers of mineral origin and organic origin. Non-limiting examples of the at least one filler may be chosen, for example, from talc, mica, silica, kaolin, Nylon (ORGASOL from Atochem), poly-β-alanine powders, polyethylene powders, TEFLON, lauroyl-lysine, starch, boron nitride, powders of tetrafluoroethylene polymers, hollow microspheres such as EXPANCEL (Nobel Industrie), POLYTAP (Dow Corning), microbeads of silicone resin (TOSPEARLS from Toshiba, for example), precipitated calcium carbonate, magnesium carbonate, magnesium hydrocarbonate, hydroxyapatite, hollow microspheres of silica (SILICA BEADS from Maprecos), glass microcapsules, ceramic microcapsules, and metallic soaps derived from carboxylic organic acids containing from 8 to 22 carbon atoms, for example, from 12 to 18 carbon atoms, such as, zinc stearate, magnesium stearate, lithium stearate, zinc laurate and magnesium myristate.

The composition according to the invention may further comprise at least one agent commonly used in cosmetics, chosen, for example, from trace elements, demulcents, sequestrants, perfumes, oils, silicones, thickeners, vitamins, proteins, ceramides, plasticizers, coalescing agents, cohesion agents, alkalinizing agents, acidifying agents, emollients and preservatives.

Of course, persons skilled in the art would be careful to select at least one of these optional additional compounds, and the amount of any of these optional additional compounds, such that the advantageous properties of the composition according to the invention are not substantially impaired by the addition envisaged.

The composition according to the invention may be prepared according to the customary methods in the fields considered.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Any numerical value inherently contains certain errors necessarily resulting from the standard deviation found in their respective testing measurements.

The following examples are intended to illustrate the invention without in anyway limiting the scope thereof.

EXAMPLE 1

A microdispersion of carnauba wax having the following composition was prepared:

| Carnauba wax | | 27 g |
|---|---|---|
| Polyoxyethylenated (30 EO) glyceryl monostearate (TAGAT S from Goldschmidt) | | 6.75 g |
| Ethanol | | 10 g |
| Water | qs | 100 g |

The wax and the surfactant were heated to 90° C. while homogenizing the mixture, with moderate stirring. While maintaining stirring, water, heated to 90° C., was then incorporated. The mixture was cooled to room temperature and ethanol was added in order to obtain a wax microdispersion having a mean particle diameter of about 170 nm.

EXAMPLE 2

A mascara having the following composition was prepared:

| Polyurethane in aqueous dispersion sold under the name AVALURE UR 425 by the company Goodrich at 49% by weight of active substances | | 14 g AS |
|---|---|---|
| Microdispersion of wax of Example 1 | | 31.5 g |
| Beeswax | | 10 g |
| Thickening agent | | 1.9 g |
| Ethanol | | 7 g |
| Propylene glycol | | 5 g |
| Pigments | | 5 g |
| Preservatives | qs | |
| Water | qs | 100 g |

The mascara was easily applied to the eyelashes and formed a make-up which was resistant to cold water. It was easily removed as make-up with hot water (40-C).

EXAMPLE 3

A mascara having the following composition was prepared:

| Sulphopolyester sold under the name EASTMAN AQ 55 S by the company Eastman | | 20.8 g AS |
|---|---|---|
| Microdispersion of wax of Example 1 | | 34.5 g |
| Hydroxyethyl cellulose | | 0.9 g |
| Propylene glycol | | 5 g |

-continued

| Pigments | | 7 g |
|---|---|---|
| Preservatives | qs | |
| Water | qs | 100 g |

What is claimed is:

1. A method for forming a film comprising applying to a keratinous material a composition comprising, in a physiologically acceptable medium comprising an aqueous phase:
   an aqueous microdispersion of particles of at least one wax, and
   an aqueous dispersion of particles of at least one film-forming polymer, wherein the film formed on the keratinous material has good resistance to cold water and can be removed with hot water.

2. A method for forming a film comprising applying to a keratinous fiber, a cosmetic composition, in a physiologically acceptable medium, comprising at least one film-forming polymer and at least one wax, wherein the film formed on the keratinous material has good resistance to cold water and can be removed with hot water.

3. A method according to claim 1, wherein said particles of at least one film-forming polymer have a mean particle size ranging from 10 to 500 nm.

4. A method according to claim 3, wherein said particles of at least one film-forming polymer have a mean particle size ranging from 20 to 300 nm.

5. A method according to claim 1, wherein said at least one film-forming polymer is chosen from free-radical polymers, polycondensates polymers and polymers of natural origin.

6. A method according to claim 5, wherein said at least one film-forming polymer is chosen from vinyl polymers, polyurethanes, polyesters and polyamides.

7. A method according to claim 6, wherein said at least one film-forming polymer is chosen from polyurethanes.

8. A method according to claim 1, wherein said at least one film-forming polymer has a water uptake of less than or equal to 50%.

9. A method according to claim 8, wherein said at least one film-forming polymer has a water uptake of less than or equal to 40%.

10. A method according to claim 9, wherein said at least one film-forming polymer has a water uptake of less than or equal to 30%.

11. A method according to claim 10, wherein said at least one film-forming polymer has a water uptake of less than or equal to 20%.

12. A method according to claim 1, wherein said at least one film-forming polymer is present in an amount ranging from 1% to 60% by weight relative to the total weight of said composition.

13. A method according to claim 12, wherein said at least one film-forming polymer is present in an amount ranging from 5% to 40% by weight relative to the total weight of said composition.

14. A method according to claim 13, wherein said at least one film-forming polymer is present in an amount ranging from 10% to 30% by weight relative to the total weight of said composition.

15. A method according to claim 1, wherein said particles of at least one wax have a mean particle size of less than 1 μm.

16. A method according to claim 15 wherein said particles of at least one wax have a mean particle size of less than 0.5 μm.

17. A method according to claim 1, wherein said at least one wax has a melting point ranging from 30° C. to 120° C.

18. A method according to claim 17, wherein said at least one wax has a melting point ranging from 45° C. to 120° C.

19. A method according to claim 1, wherein said at least one wax is chosen from polar waxes, silicone waxes, and fluorinated waxes.

20. A method according to claim 19, wherein said polar waxes are chosen from hydrocarbon waxes, and waxes formed from catalytic hydrogenation of oils.

21. A method according to claim 20, wherein said hydrocarbon waxes are chosen from beeswax, lanolin wax, Chinese waxes, rice wax, Carnauba wax, candelilla wax, ouricury wax, cork fiber wax, sugarcane wax, Japan wax, sumac wax; montan wax, waxy copolymers and esters thereof.

22. A method according to claim 20, wherein said waxes formed from catalytic hydrogenation of oils are formed from oils chosen from animal oils containing linear and branched ($C_8$–$C_{12}$) fatty chains and vegetable oils containing linear and branched ($C_6$–$C_{12}$) fatty chains.

23. A method according to claim 20, wherein said waxes formed from catalytic hydrogenation of oils are chosen from hydrogenated jojoba oil, hydrogenated sunflower oil, hydrogenated castor oil, hydrogenated copra oil and hydrogenated lanolin oil.

24. A method according to claim 1, wherein said at least one wax has a hardness ranging from 0.05 MPa to 15 MPa.

25. A method according to claim 24, wherein said at least one wax has a hardness ranging from 3 MPa to 15 MPa.

26. A method according to claim 1, wherein said at least one wax is present in a dry matter content ranging from 0.1% to 50% by weight relative to the total weight of said composition.

27. A method according to claim 26, wherein said at least one wax is present in a dry matter content ranging from 1% to 30% by weight relative to the total weight of said composition.

28. A method according to claim 27, wherein said at least one wax is present in a dry matter content ranging from 5% to 20% by weight relative to the total weight of said composition.

29. A method according to claim 1, wherein said composition further comprises at least one fatty additive chosen from fatty oily additives, fatty pasty additives, and fat-soluble active ingredients.

30. A method according to claim 29, wherein said fat-soluble active ingredients are chosen from UV-screening agents, fat-soluble vitamins, and fat-soluble cosmetic active agents.

31. A method according to claim 1, wherein said composition further comprises at least one surfactant.

32. A method according to claim 31, wherein said at least one surfactant is chosen from:
anionic surfactants chosen from optionally unsaturated fatty acid salts having 12 to 18 carbon atoms, alkali metal salts of salts of organic bases with ($C_{12}$–$C_{18}$) alkylsulfuric acids, alkali metal salts of salts of organic bases with ($C_{12}$–$C_{18}$) alkylsulfonic acids, alkali metal salts of salts of organic bases with ($C_6$–$C_{18}$) alkylarylsulfonic acids, and ether sulfates;
nonionic surfactants, chosen from polyalkoxylated surfactants, polyglycerolated surfactants, esters of fatty acids and polyols, alkanediols, alkyl ethers of alkanediols; and at least one compound chosen from alkyl carbamates of triglycerol, oxyethylenated derivatives of lanolin alcohols, propoxylated derivatives of lanolin alcohols, and lanolin fatty acids; and
cationic surfactants, chosen from quaternary ammonium derivatives.

33. A method according to claim 31, wherein said at least one surfactant is present in an amount ranging from 0.01% to 5% by weight relative to the total weight of said composition.

34. A method according to claim 1, wherein the weight ratio of said at least one film-forming polymer to at least one wax ranges from 50:50 to 95:5.

35. A method according to claim 34, wherein the weight ratio of said at least one film-forming polymer to at least one wax ranges from 60:40 to 80:20.

36. A method according to claim 1, wherein said composition further comprises at least one additional water-soluble film-forming polymer.

37. A method according to claim 36, wherein said at least one additional water-soluble film-forming polymer is chosen from water-soluble cellulosic polymers, keratin derivatives, chitins, chitosan derivatives, cellulose derivatives, acrylic polymers, acrylic copolymers, polyvinyl alcohols, polyvinyl pyrrolidones, vinyl copolymers, polyethylene glycols and optionally modified polymers of natural origin.

38. A method according to claim 1, wherein said composition further comprises particles of at least one additional wax having a particle size of at least 1 μm, further wherein said particles of at least one additional wax is dispersed in said aqueous phase.

39. A method according to claim 38, wherein said particles of at least one additional wax have a particle size ranging from 1 μm to 10 μm.

40. A method according to claim 1, wherein said composition further comprises at least one agent chosen from trace elements, demulcents, sequestrants, perfumes, oils, silicones, thickeners, vitamins, proteins, ceramides, plasticizers, coalescing agents, cohesion agents, alkalinizing agents, acidifying agents, emollients and preservatives.

41. A method according to claim 1, wherein said composition further comprises at least one pulverulent compound chosen from pigments and pearlescent agents.

42. A method according to claim 1, wherein said composition further comprises at least one filler.

43. A mascara comprising:
an aqueous microdispersion of particles of at least one wax, and
an aqueous dispersion of particles of at least one film-forming polymer,
wherein said particles of at least one film-forming polymer have a mean particle size of at least 10 nm and further wherein said at least one film-forming polymer is not a coloring polymer.

44. A mascara according to claim 43, wherein said particles of at least one film-forming polymer have a mean particle size ranging from 10 to 500 nm.

45. A mascara according to claim 44, wherein said particles of at least one film-forming polymer have a mean particle size ranging from 20 to 300 nm.

46. A mascara according to claim 43, wherein said at least one film-forming polymer is chosen from free-radical polymers, polycondensates polymers and polymers of natural origin.

47. A mascara according to claim 46, herein said at least one film-forming polymer is chosen from vinyl polymers, polyurethanes, polyesters and polyamides.

48. A mascara according to claim 43, wherein said at least one film-forming polymer is chosen from polyurethanes.

49. A mascara according to claim 43, wherein said at least one film-forming polymer has a water uptake of less than or equal to 50%.

50. A mascara according to claim 49, wherein said at least one film-forming polymer has a water uptake of less than or equal to 40%.

51. A mascara according to claim 50, wherein said at least one film-forming polymer has a water uptake of less than or equal to 30%.

52. A mascara according to claim 51, wherein said at least one film-forming polymer has a water uptake of less than or equal to 20%.

53. A mascara according to claim 43, wherein said at least one film-forming polymer is present in an amount ranging from 1% to 60% by weight relative to the total weight of said mascara.

54. A mascara according to claim 53, wherein said at least one film-forming polymer is present in an amount ranging from 5% to 40% by weight relative to the total weight of said mascara.

55. A mascara according to claim 54, wherein said at least one film-forming polymer is present in an amount ranging from 10% to 30% by weight relative to the total weight of said mascara.

56. A mascara according to claim 43, wherein said particles of at least one wax have a mean particle size of less than 1 μm.

57. A mascara according to claim 56, wherein said particles of at least one wax have a mean particle size of less than 0.5 μm.

58. A mascara according to claim 43, wherein said at least one wax has a melting point ranging from 30° C. to 120° C.

59. A mascara according to claim 58, wherein said at least one wax has a melting point ranging from 45° C. to 120° C.

60. A mascara according to claim 43, wherein said at least one wax is chosen from polar waxes, silicone waxes, and fluorinated waxes.

61. A mascara according to claim 60, wherein said polar waxes are chosen from hydrocarbon waxes, and waxes formed from catalytic hydrogenation of oils.

62. A mascara according to claim 61, wherein said hydrocarbon waxes are chosen from beeswax, lanolin wax, Chinese waxes, rice wax, Carnauba wax, candelilla wax, ouricury wax, cork fiber wax, sugarcane wax, Japan wax, sumac wax, montan wax, waxy copolymers and esters of waxes.

63. A mascara according to claim 61, wherein said waxes formed from catalytic hydrogenation of oils are formed from oils chosen from animal oils containing linear and branched ($C_8$–$C_{12}$) fatty chains and vegetable oils containing linear and branched ($C_8$–$C_{12}$) fatty chains.

64. A mascara according to claim 61, wherein said waxes formed from catalytic hydrogenation of oils are chosen from hydrogenated jojoba oil, hydrogenated sunflower oil, hydrogenated castor oil, hydrogenated copra oil and hydrogenated lanolin oil.

65. A mascara according to claim 43, wherein said at least one wax has a hardness ranging from 0.05 MPa to 15 MPa.

66. A mascara according to claim 65, wherein said at least one wax has a hardness ranging from 3 MPa to 15 MPa.

67. A mascara according to claim 43, wherein said at least one wax is present in a dry matter content ranging from 0.1% to 50% by weight relative to the total weight of said mascara.

68. A mascara according to claim 67, wherein said at least one wax is present in a dry matter content ranging from 1% to 30% by weight relative to the total weight of said mascara.

69. A mascara according to claim 68, wherein said at least one wax is present in a dry matter content ranging from 5% to 20% by weight relative to the total weight of said mascara.

70. A mascara according to claim 43, wherein said mascara further comprises at least one fatty additive chosen from fatty oily additives, fatty pasty additives, and fat-soluble active ingredients.

71. A mascara according to claim 70, wherein said fat-soluble active ingredients are chosen from UV-screening agents, fat-soluble vitamins, and fat-soluble cosmetic active agents.

72. A mascara according to claim 43, wherein said mascara further comprises at least one surfactant.

73. A mascara according to claim 72, wherein said at least one surfactant is chosen from:
  anionic surfactants chosen from optionally unsaturated fatty acid salts having 12 to 18 carbon atoms, alkali metal salts of salts of organic bases with ($C_{12}$–$C_{18}$) alkylsulfuric acids, alkali metal salts of salts of organic bases with ($C_{12}$–$C_{18}$) alkylsulfonic acids, alkali metal salts of salts of organic bases with ($C_6$–$C_{18}$) alkylarylsulfonic acids, and ether sulfates;
  nonionic surfactants, chosen from polyalkoxylated surfactants, polyglycerolated surfactants, esters of fatty acids and polyols, alkanediols, alkyl ethers of alkanediols, and at least one compound chosen from alkyl carbamates of triglycerol, oxyethylenated derivatives of lanolin alcohols, propoxylated derivatives of lanolin alcohols, and lanolin fatty acids; and
  cationic surfactants, chosen from quaternary ammonium derivatives.

74. A mascara according to claim 72, wherein said at least one surfactant is present in an amount ranging from 0.01% to 5% by weight relative to the total weight of said mascara.

75. A mascara according to claim 43, wherein the weight ratio of said at least one film-forming polymer to at least one wax ranges from 50:50 to 95:5.

76. A mascara according to claim 75, wherein the weight ratio of said at least one film-forming polymer to at least one wax ranges from 60:40 to 80:20.

77. A mascara according to claim 43, wherein said mascara further comprises at least one additional water-soluble film-forming polymer.

78. A mascara according to claim 77, wherein at least one additional water-soluble film-forming polymer is chosen from water-soluble cellulosic polymers, keratin derivatives, chitins, chitosan derivatives, cellulose derivatives, acrylic polymers, acrylic copolymers, polyvinyl alcohols, polyvinyl pyrrolidones, vinyl copolymers, polyethylene glycols and optionally modified polymers of natural origin.

79. A mascara according to claim 43, wherein said mascara further comprises particles of at least one additional wax having a particle size of at least 1 μm, wherein said particles of at least one additional wax is dispersed in said aqueous phase.

80. A mascara according to claim 79, wherein said particles of at least one additional wax have a particle size ranging from 1 μm to 10 μm.

81. A mascara according to claim 43, wherein said mascara further comprises at least one agent chosen from trace elements, demulcents, sequestrants, perfumes, oils, silicones, thickeners, vitamins, proteins, ceramides, plasticizers, coalescing agents, cohesion agents, alkalinizing agents, acidifying agents, emollients and preservatives.

82. A mascara according to claim 43, wherein said mascara further comprises at least one pulverulent compound chosen from pigments and pearlescent agents.

83. A mascara according to claim 43, wherein said mascara further comprises at least one filler.

84. A mascara according to claim 43, wherein said at least one wax has a hardness ranging from 3 MPa to 15 MPa.

85. A cosmetic method of using make-up or nontherapeutic care comprising:
applying to a keratinous material a mascara comprising, in a physiologically acceptable medium comprising an aqueous phase:
an aqueous microdispersion of particles of at least one wax, and
an aqueous dispersion of particles of at least one film-forming polymer,
wherein said particles of at least one film-forming polymer have a mean particle size of at least 10 nm and further wherein said at least one film-forming polymer is not a coloring polymer.

86. A cosmetic method according to claim 85, wherein said keratinous material is an eyelash.

* * * * *

UNITED STATES PATENT AND TRADEMARK OFFICE
CERTIFICATE OF CORRECTION

PATENT NO. : 6,946,123 B2
DATED : September 20, 2005
INVENTOR(S) : Valérie De La Poterie et al.

It is certified that error appears in the above-identified patent and that said Letters Patent is hereby corrected as shown below:

Column 14,
Line 18, "keratinous fiber," should read -- keratinous material --; and after "composition", insert -- comprising --.
Line 19, after "medium," and before "at least one", delete "comprising".
Line 20, after "polymer and", insert -- an aqueous microdispersion of particles of --.
Line 31, "polycondesates polymers" should read -- polycondensate polymers --.
Line 65, after "claim 15", insert a comma.

Column 15,
Line 20, "$(C_6-C_{12})$" should read -- $(C_8-C_{12})$ --.

Column 16,
Line 58, "polycondensates polymers" should read -- polycondensate polymers --.

Signed and Sealed this

Twenty-first Day of February, 2006

JON W. DUDAS
*Director of the United States Patent and Trademark Office*